United States Patent
Board

(10) Patent No.: US 6,684,700 B1
(45) Date of Patent: *Feb. 3, 2004

(54) STRESS WAVE SENSOR

(75) Inventor: David B. Board, Boca Raton, FL (US)

(73) Assignee: Swantech, L.L.C., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/636,697

(22) Filed: Aug. 11, 2000

(51) Int. Cl.⁷ .......................... G01N 29/00; G06F 19/00
(52) U.S. Cl. ............................ 73/579; 73/582; 73/599; 702/56
(58) Field of Search ................... 73/579, 597, 598, 73/599, 600, 602, 584, 593, 660, 662, 659, 587; 702/56

(56) References Cited

U.S. PATENT DOCUMENTS

| | | | |
|---|---|---|---|
| 3,554,012 A | 1/1971 | Sohoel | 73/67.2 |
| 3,842,663 A * | 10/1974 | Harting et al. | 73/593 |
| 3,924,456 A * | 12/1975 | Vahaviolos | 73/770 |
| 4,207,771 A * | 6/1980 | Carlos et al. | 73/587 |
| 4,429,578 A | 2/1984 | Darrel et al. | 73/659 |
| 4,530,240 A | 7/1985 | Board et al. | 73/593 |
| 5,004,985 A * | 4/1991 | Holroyd et al. | 324/727 |
| 5,005,142 A | 4/1991 | Lipchak et al. | 364/550 |
| 5,043,736 A | 8/1991 | Darnell et al. | 342/357 |
| 5,101,162 A * | 3/1992 | Webster et al. | 324/618 |
| 5,115,671 A | 5/1992 | Hicho | 73/488 |
| 5,210,704 A | 5/1993 | Husseiny | 364/551.02 |
| 5,239,468 A | 8/1993 | Sewersky et al. | 364/424.03 |
| 5,309,379 A | 5/1994 | Rawlings et al. | 364/578 |
| 5,333,240 A | 7/1994 | Matsumoto et al. | 395/23 |
| 5,365,787 A | 11/1994 | Hernandez et al. | 73/660 |
| RE34,975 E * | 6/1995 | Orban et al. | 367/34 |
| 5,566,092 A | 10/1996 | Wang et al. | 364/551.02 |
| 5,581,016 A * | 12/1996 | Gonzalez et al. | 73/35.06 |

(List continued on next page.)

OTHER PUBLICATIONS

Xu et al., "An ANS Based Helicopter Transmission Diagnostic System," IEEE, 8/97.

Yen, "Health Monitoring of Vibration Signatures," IEEE, date unknown—(Since date unknown cited in an abundance of caution).

(List continued on next page.)

*Primary Examiner*—Hezron Williams
*Assistant Examiner*—Jacques Saint-Surin
(74) *Attorney, Agent, or Firm*—Malin, Haley & DiMaggio, P.A.

(57) ABSTRACT

A sensor is disclosed specifically for detecting stress waves for use in a stress wave analysis system. The stress waves are preferably detected in a narrow frequency range of 35–40KHz. At this range, stress waves from friction and impact sources typically propagate through machine structures at detectable amplitudes. In order to maximize the signal to noise ratio of stress waves, relative to background noise and vibration, the sensor of the present invention is designed and calibrated with a frequency response and damping features that are specifically tailored for stress wave analysis. The sensor preferably satisfies the following three criteria: (a) has a resonant gain of approximately 30 db, at its primary resonant frequency, to assure adequate selective amplification of stress waves; (b) provide a total energy content of the Resonant Energy Integral within a specified tolerance band and which can be measurable using standard test equipment and fixtures to produce calibration data that is traceable to recognized standards; and (c) have its resonant peak amplitude output decay to half amplitude by five cycles, and be down to no more than twenty percent of the initial response in the number of cycles that occur during the time period that corresponds to the corner frequency of a low pass filter.

22 Claims, 9 Drawing Sheets

U.S. PATENT DOCUMENTS

| | | | |
|---|---|---|---|
| 5,602,761 A | | 2/1997 | Spoerre et al. ............. 364/554 |
| 5,608,845 A | | 3/1997 | Ohtsuka et al. ............... 395/50 |
| 5,659,136 A | * | 8/1997 | Koch et al. .................... 73/462 |
| 5,734,087 A | * | 3/1998 | Yamashita .................. 73/1.15 |
| 5,852,793 A | * | 12/1998 | Board et al. .................. 702/56 |
| 5,875,420 A | | 2/1999 | Piety et al. ................. 702/182 |
| 5,952,587 A | | 9/1999 | Rhodes et al. ......... 73/862.541 |
| 6,076,405 A | | 6/2000 | Schoess ....................... 73/587 |

OTHER PUBLICATIONS

Yen et al., "Health Monitoring of Vibration Signatures in Rotorcraft Wings," IEEE, date unknown—(Since date unknown cited in an abundance of caution).

Marciano et al., "Mechanical System Condition Monitor (MSCM) System Design," IEEE, 8/90.

* cited by examiner

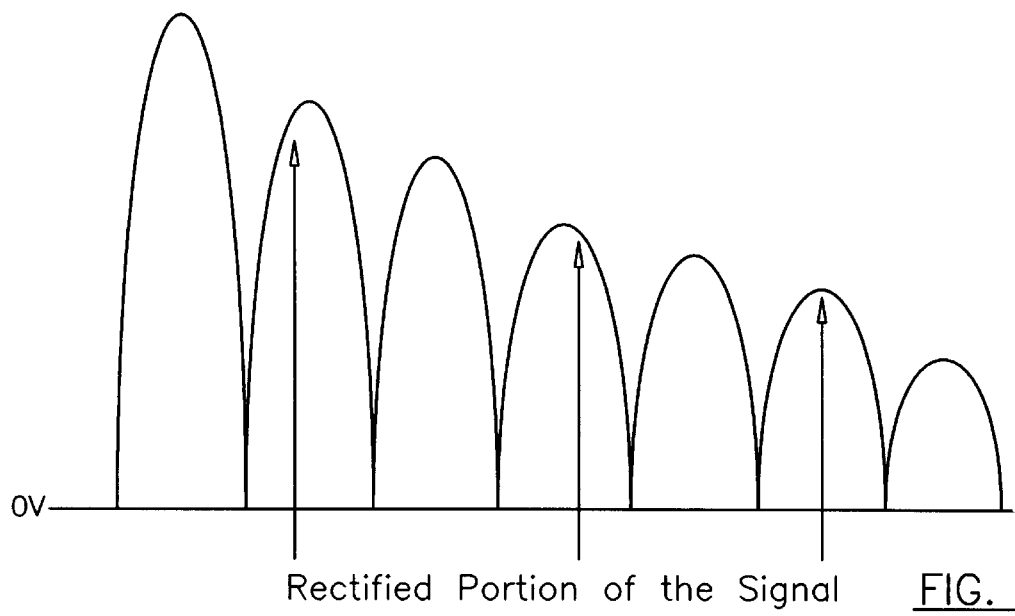
Rectified Portion of the Signal      FIG. 8
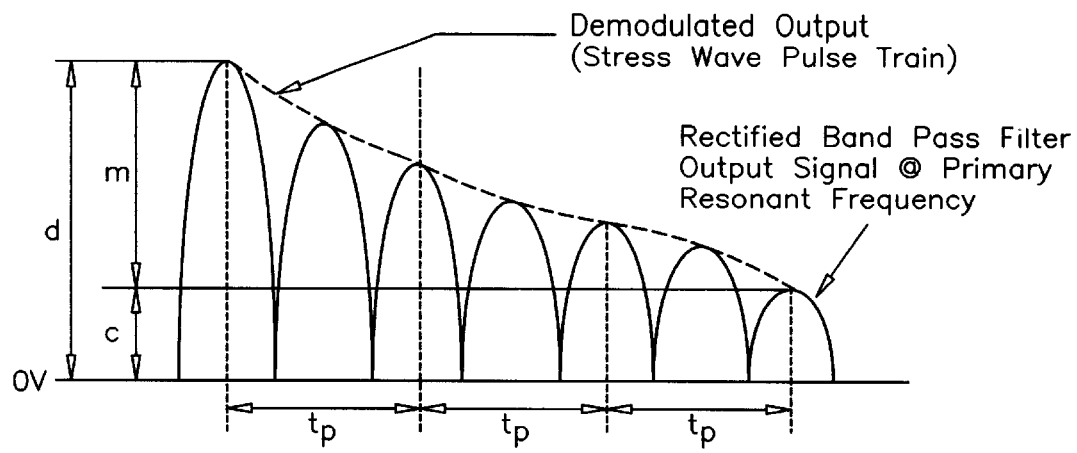
$t_p$ = 1/40000 cps = .000025 seconds
$3t_p$ = .000075 seconds
$5t_p$ = .000125 seconds
$8t_p$ = .0002 seconds
FIG. 9

- - - - - - - - Stress Wave Pulse Train
m = modulation amplitude
$8t_p$ = 1 cycle of a Stress Wave Pulse Train = 5000 Hz

STRESS WAVE SENSOR

BACKGROUND OF THE INVENTION

1. Field of the Invention

The present invention is generally directed to sensors and particularly to sensors used in stress wave analysis.

2. Description of Related Art

Stress wave analysis is an ultrasonic instrumentation technique which is used for measurement of friction and shock in mechanical devices. Stress waves are in the form of high frequency structure borne sounds caused by friction between moving parts. The analysis of the stress waves involves the detection and amplification of the high frequency sounds. In addition to the high frequency sounds, other noises and vibration signals are also present, which are not directly related to the stress waves. However, these other signals can interfere with proper analysis of any stress waves emitted by a mechanical device and should be eliminated.

Past attempts at stress wave analysis have incorporated specially selected piezoelectric accelerometers as stress wave sensors. However, these transducers are not specifically designed to detect stress waves, and suffer important shortcomings relative to Analog Signal. Conditioning ("ASC") and Digital Signal Processing ("DSP") elements of stress wave analysis instrumentation, such as those shown in FIG. 1.

An accelerometer, when used as a stress wave sensor, is often selected to have maximum repeatability of its primary resonant frequency between 30 Khz and 40 Khz, and its sensitivity at the primary resonant frequency. When secondary resonances are also present in the sensor's frequency response, they are often very difficult, if not impossible, to eliminate or control, with the same precision as the primary resonance as shown in FIG. 2. Efforts to adjust or control these secondary resonances may also cause unintended and undesirable changes in the sensitivity of the primary resonance.

Accordingly, what is needed in the art is a sensor having characteristics that receives stress wave signals while discarding background noises and vibrations. It is therefore to the effective resolution of the shortcomings of the prior art that the present invention is directed.

BRIEF SUMMARY OF THE INVENTION

The present invention relates to a sensor having characteristics designed specifically for detecting stress waves for use in a stress wave analysis system. In order to eliminate vibration, audible noise and acoustic emission sources that are not directly related to friction and mechanical impact events in operating machinery, it is preferred, to detect stress waves in a narrow frequency range, such as, but not limited to, 35 Khz to 40 KHz. At this frequency range, stress waves from friction and impact sources typically propagate through machine structures at detectable amplitudes. Thus, in order to maximize the signal to noise ratio of stress waves, relative to background noise and vibration, the sensor of the present invention is designed and calibrated with a frequency response and damping characteristics that are specifically tailored for stress wave analysis.

The sensor of the present invention preferably satisfies the following three criteria:

(a) has a resonant gain of approximately 30 db, at its primary resonant frequency, to assure adequate selective amplification of stress waves;

(b) provide a total energy content of the Resonant Energy Integral within a specified tolerance band (i.e. +/−10% of a standard value) and which can be measurable using standard test equipment and fixtures to produce calibration data that is traceable to recognized standards; and (c) have its resonant output decay to half amplitude in five cycles or less, and be down to no more than twenty (20%) percent of the initial response in the number of cycles that correspond to the corner frequency of the band pass filter.

Accordingly, it is an object of the present invention to provide a sensor having a frequency response and damping characteristics specifically designed for stress wave analysis.

In accordance with these and other objects which will become apparent hereinafter, the instant invention will now be described with particular reference to the accompanying drawings.

BRIEF DESCRIPTION OF THE SEVERAL VIEWS OF THE DRAWINGS

FIG. 8 is a graph illustrating a rectified band-pass filter output in accordance with the present invention;

FIG. 9 is a graph illustrating a demodulator output in accordance with the present invention;

DETAILED DESCRIPTION OF THE INVENTION

Figure 12:
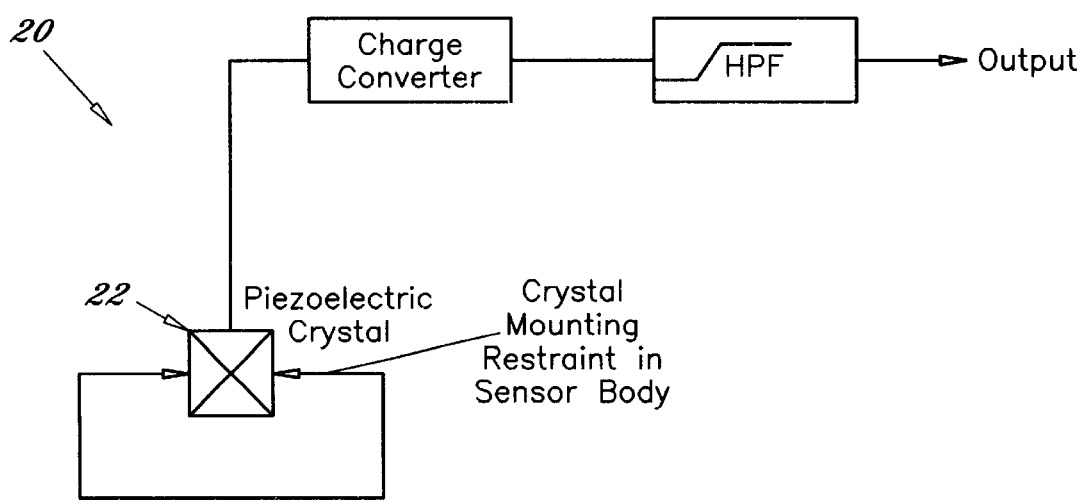
FIG. 12 is a block diagram of one embodiment for the stress wave sensor of the present invention.

The various characteristics of the present invention stress wave sensor are illustrated in the Figures, with FIG. 12 illustrating one embodiment for the components of the stress wave sensor. The stress wave sensor in accordance with the present invention is generally designated as reference numeral 20.

The amplitude of stress waves is relatively small as compared to low frequency sources of vibration and audible sound. As such, it is preferred to selectively amplify signals in a desired frequency range (i.e. 35–40 KHz) which are associated with stress wave signals. The chosen frequency range is preferably well above structural vibration frequencies, which are commonly between 0 to 20 KHz. The chosen frequency range is also preferably within the range of standard test equipment, and below high frequency acoustic emission sources, which are typically occurring at frequencies over 100 KHz.

Though within the scope of the invention, it is not desirable to selectively amplify the stress wave signals electronically, as such techniques also amplify undesired background noise from the noise floor of the electronic circuitry.

Thus, to maximize the stress wave signal to noise ratio of stress wave sensor 20, the transducing element 22 of sensor 20 is designed to have a primary resonant frequency preferably between 35 KHz and 40 KHz. By choosing this preferred frequency range for the resonant response, the desired selective amplification can be accomplished by mechanical means, prior to conversion to an electrical signal which is further processed by ASC and DSP techniques. To assure sufficient selective amplification of the stress wave signals for many common types of machinery, the resonant gain is preferably approximately 30 db. This resonant gain is defined as the ratio of the sensitivity at the primary resonance to the sensitivity at frequencies below 20 KHz.

Figure 1:
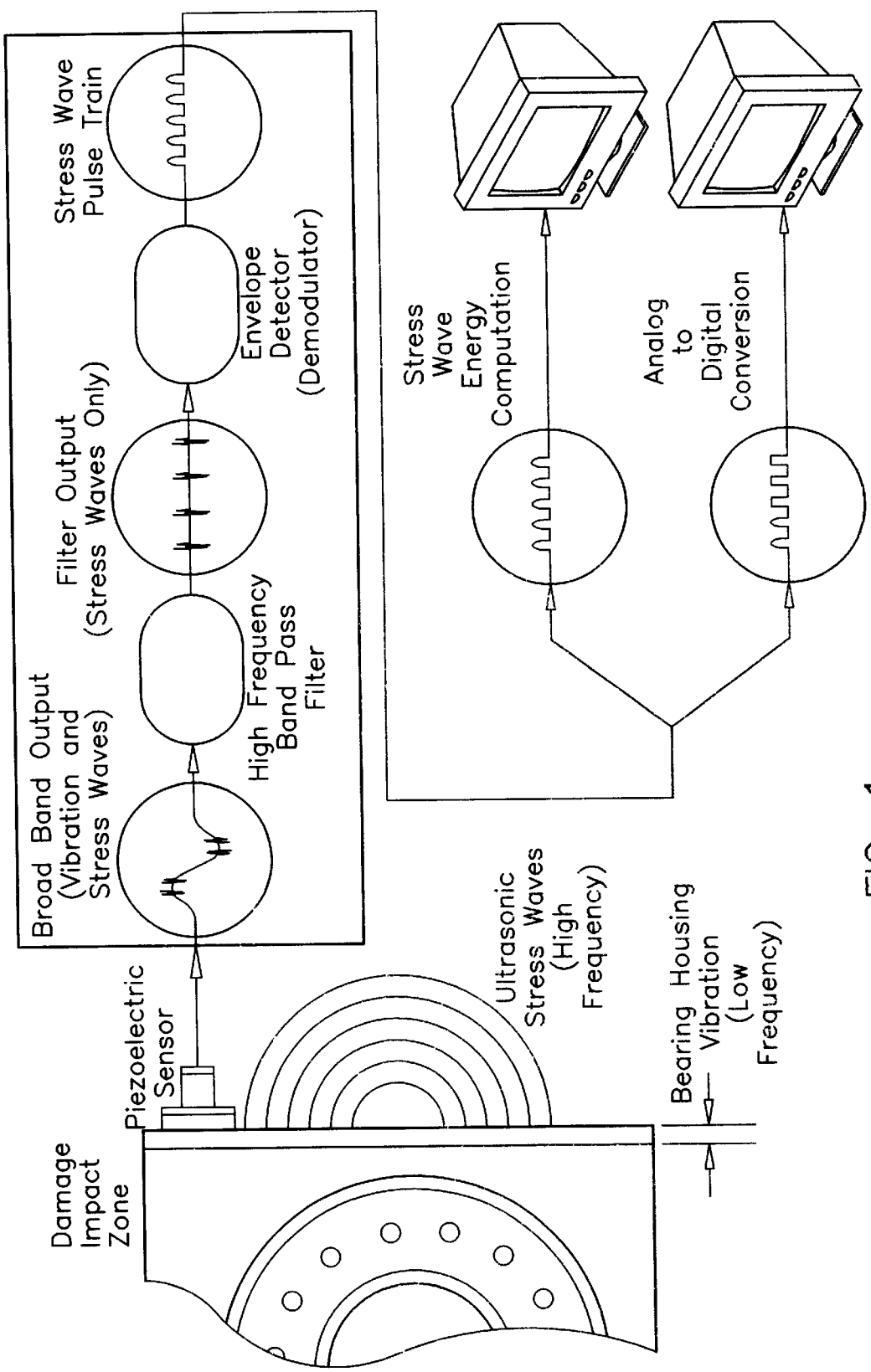
FIG. 1 is a block diagram of a stress wave analysis system including the., stress wave sensor of the present invention.
Figure 2:
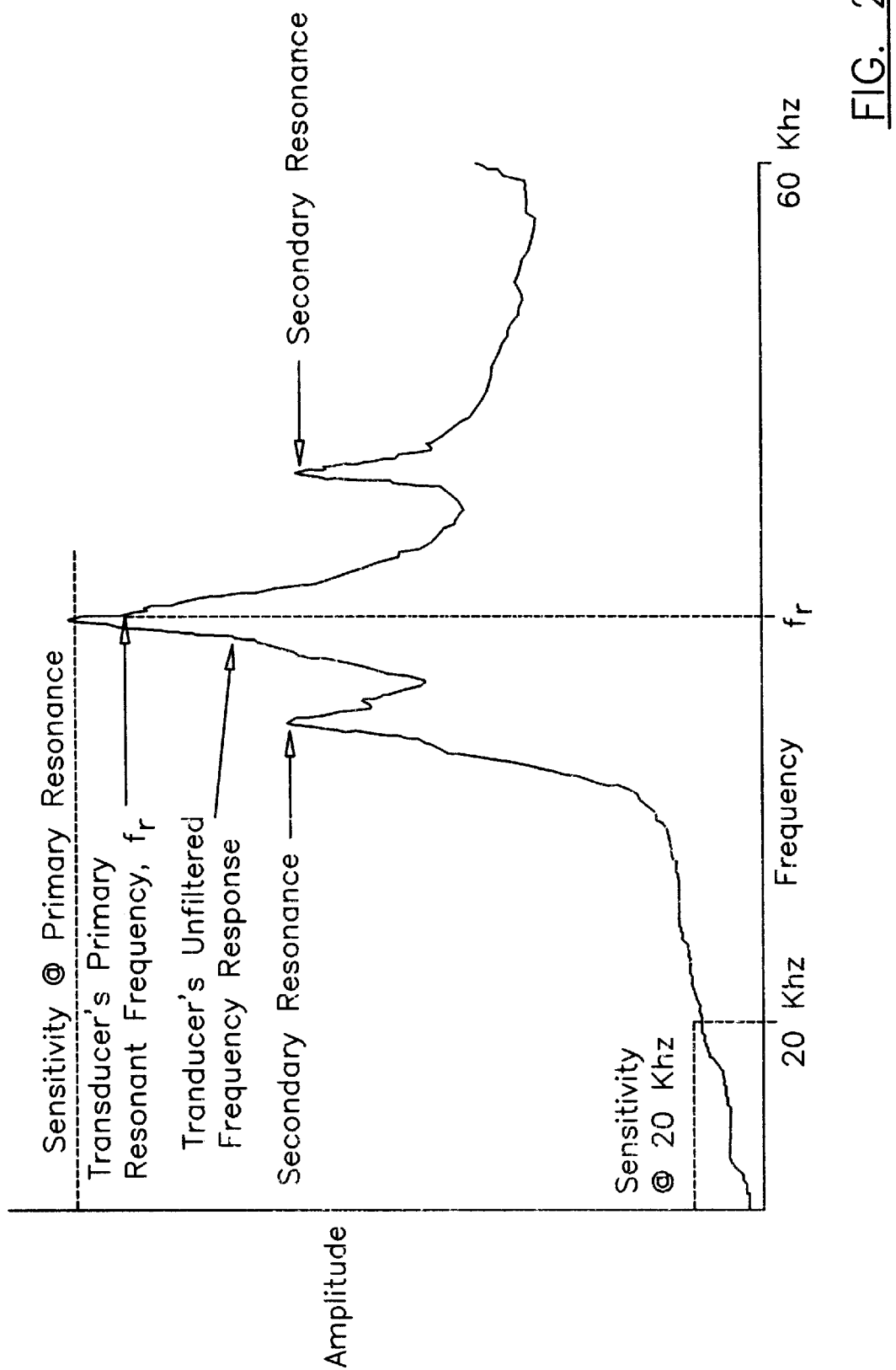
FIG. 2 is a graph illustrating a stress wave sensor frequency response in accordance with the present invention.
Figure 3:
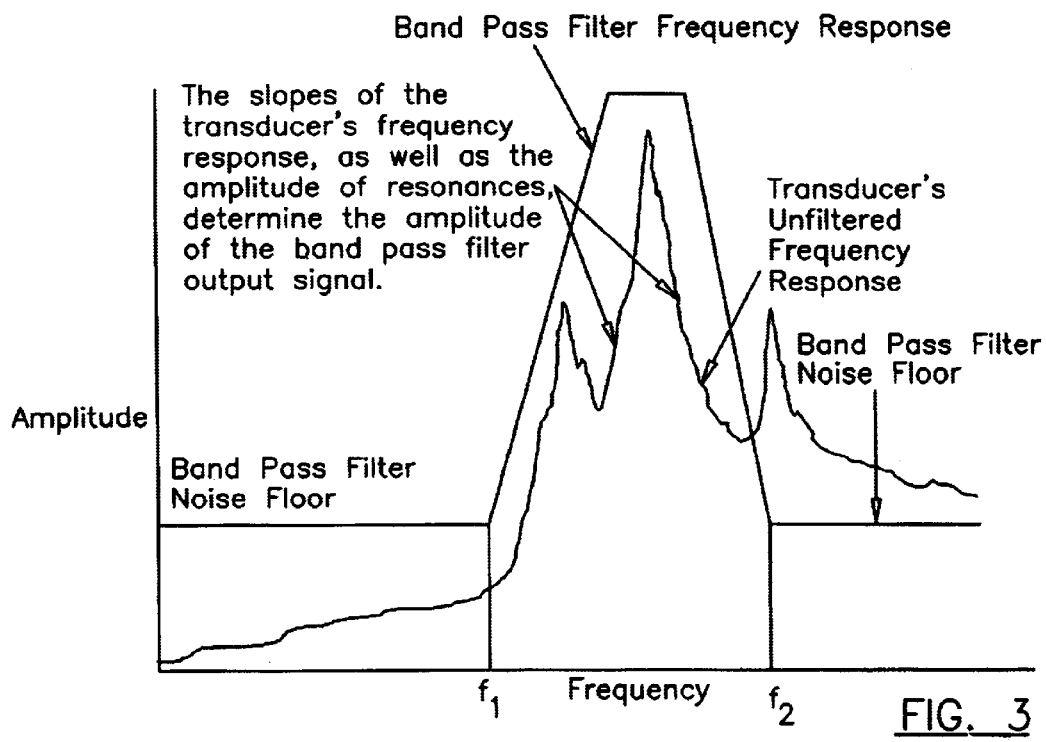
FIG. 3 is a graph illustrating a stress wave sensor frequency response and a band-pass filter response in accordance with the present invention.

As seen in FIG. 3, the secondary resonances which may be present in a sensor 20's frequency response may fall within the frequency response curve of a band pass filter ("BPF"), and thus can result in undesirable sensor-to-sensor amplitude variations of a filtered and demodulated stress wave pulse train ("SWPT").

Figure 4:
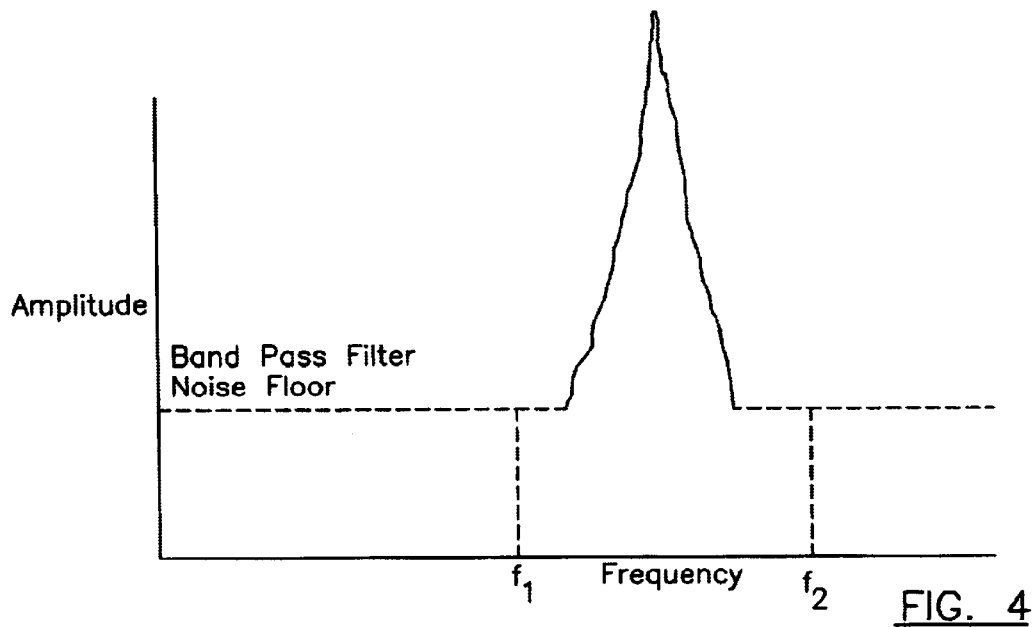
FIG. 4 is a graph illustrating a filtered sensor frequency response in accordance with the present invention.

Another important factor in a stress wave sensor's performance is the overall shape of its frequency response curve. As also seen in FIG. 3, the slopes of the sensor's resonant frequency response, as well as the amplitude of the resonances, determine the amplitude of the BPF's output. The BPF has a relatively flat response between 35 KHz and 40 KHz, and a steep roll-off above and below the pass band, down to the noise floor of the BPF circuitry. From FIG. 3, the frequency where the high pass roll-off intersects the noise floor can be designated $f_1$, and the frequency where the low pass roll-off intersects the noise floor can be designated $f_2$. As seen in FIG. 4, the output of the BPF preferably contains no low frequency signals due to the dynamic response of machine structures (vibration) or audible noise below $f_1$, and no high frequency signals from sources of acoustic emission or secondary resonances at frequencies greater than $f_2$.

Figure 5:
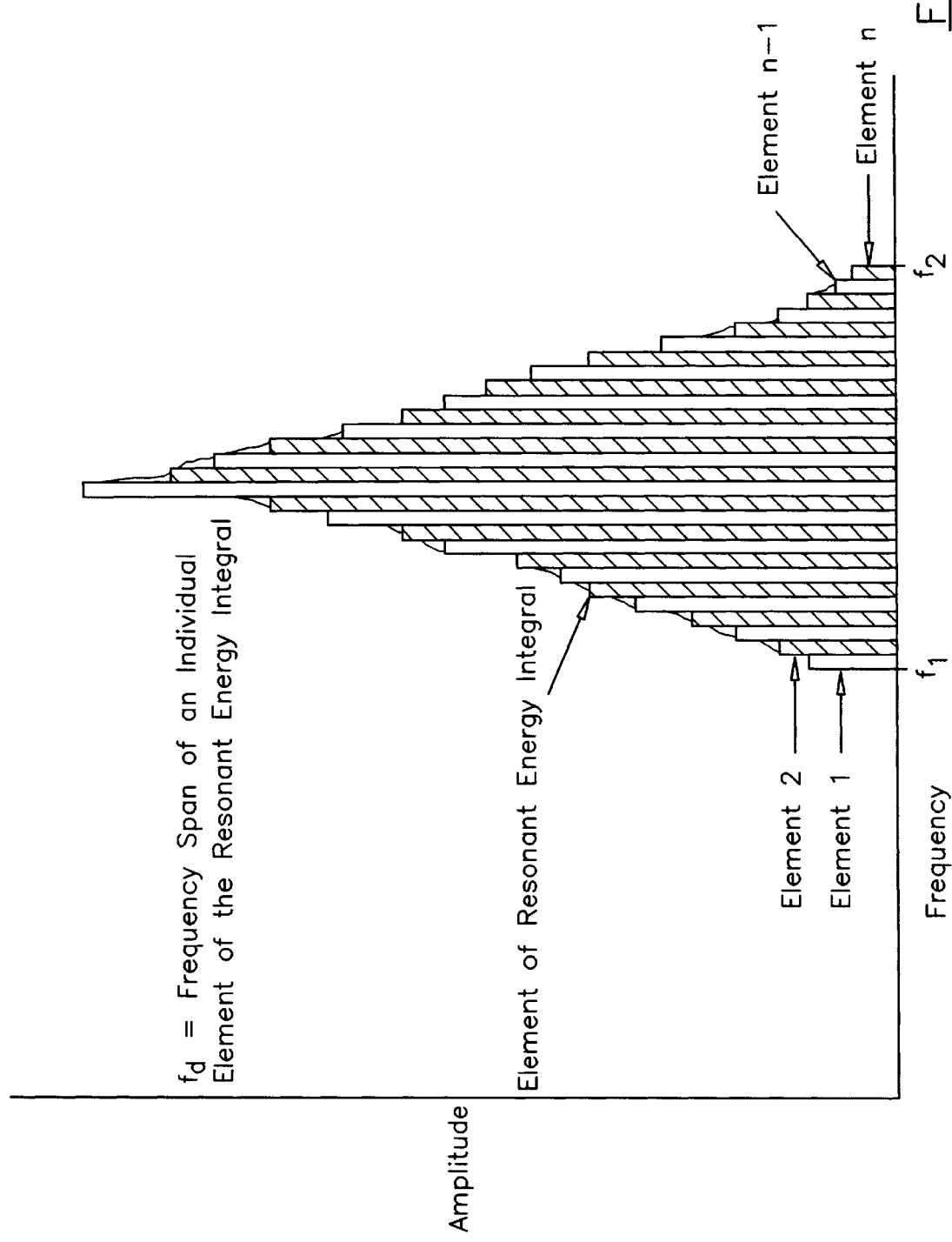
FIG. 5 is a graph illustrating a resonant energy integral in accordance with the present invention.

Preferably, stress wave sensors 20 in accordance with the present invention have sensor-to-sensor repeatability within a specified or predetermined range, which in one embodiment can be plus or minus ten (10%) percent, though such range is not considered limiting and other ranges can be used and are considered within the scope of the invention. Additionally, manufacturing and testing process also preferably produce sensors 20 with calibration data that is traceable to recognized standards, when using standard test equipment and fixtures. Thus, a standard method and stimulating each sensor 20 and measuring its output over the frequency range $f_1$ to $f_2$ is preferably devised and applied by the present invention. For creating a standard method of stimulating each sensor 20, a Resonant Energy Integral (FIG. 5) can be developed.

After assembly, each sensor 20 is preferably placed on a conventional; shaker table commonly used by accelerometer manufacturers. The shaker is preferably set at a specified or predetermined frequency and excites a sensor or unit under test ("UUT") by moving sensor 20 up and down at an amplitude that is preferably equal or approximate to a previously determined reference "g" level of acceleration. Sensor 20's output is measured and preferably recorded as a value "y", which is provided in millivolts per g (mv/g). The excitation frequency of the shaker, is preferably incrementally changed, the amplitude adjusted to achieve the reference "g" level, and another mv/g output value measurement is recorded. This process is repeated at a number ("n"), which can be predetermined, of discrete frequencies over a frequency band ranging from frequency $f_1$ to frequency $f_2$. The repeated process provides the tested sensor 20's frequency response curve over the frequency band $f_1$ to $f_2$.

Once the frequency response curve is determined, the Resonant Energy Integral can be computed preferably using a multi-step process. This process preferably consists of the following steps:

(1) sensor 20's sensitivity at each excitation frequency ("$s_n$") is multiplied by an attenuation factor ($A_{bpf}$). The attenuation factor represents the amount of signal attenuation at the particular frequency due to the frequency response of the BPF. The resultant value from the multiplication is the adjusted sensitivity ("$S_{na}$") at frequency $f_n$. In equation form the following step is represented as:

$$S_{na}=(A_{bpf})(S_n)$$

(2) adjusted sensitivity $S_{na}$ is multiplied by the frequency span ("$f_d$") of the individual element of the Resonant Energy Integral that has $f_n$ at its center. The resultant value from the multiplication is the resonant energy of the nth element of the Resonant Energy Integral. In equation form the following step is represented as:

$$E_m=(S_{na})(f_d)$$

(3) computing the total energy content of the Resonant Energy Integral by summing all of the individual $E_m$ values for elements 1 through n.

This calculated total energy content of the Resonant Energy Integral represents a preferred measure, and most likely best measurement, of the overall signal output from the band pass filter section of the stress wave analysis ASC.

Figure 6:
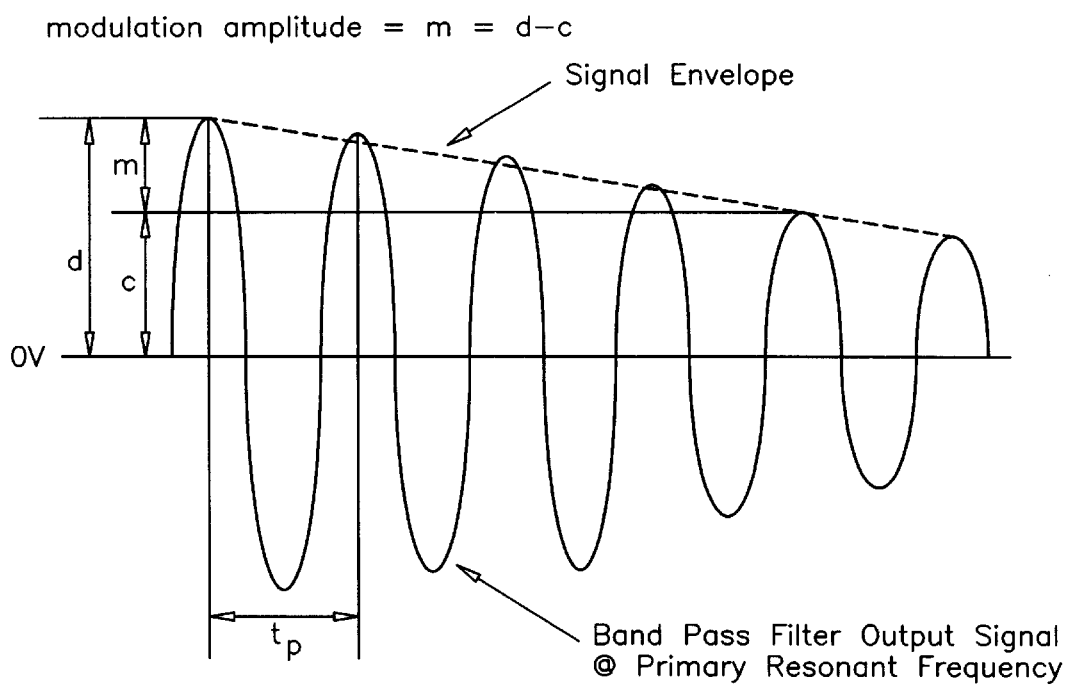
FIG. 6 is a graph illustrating "under damping" of a stress wave signal at its resonant frequency in accordance with the present invention.

As seen in FIG. 6, the band pass filter output is dominated by the primary resonant frequency. FIG. 6 illustrates the time domain response of stress wave sensor 20's filtered output, due to a single, short duration friction or shock event. The resonant output signal is essentially a damped sign wave that preferably begins at a near zero peak to peak ("p-p") amplitude. When stress waves caused by a high amplitude friction event reach sensor 20, sensor 20 is excited to a zero to peak ("0-p") amplitude of value "d". . After a sufficient number of cycles, sensor 20's amplitude decays back down to its original near zero p-p amplitude. The period of one complete cycle "$t_p$", is the reciprocal of the primary resonant frequency $f_r$. Where the primary resonant frequency is 40 KHz, the following period is calculated as:

$$T_p=1/f_r=1/40,000 cycles/sec=0.000025 sec.$$

Figure 7:
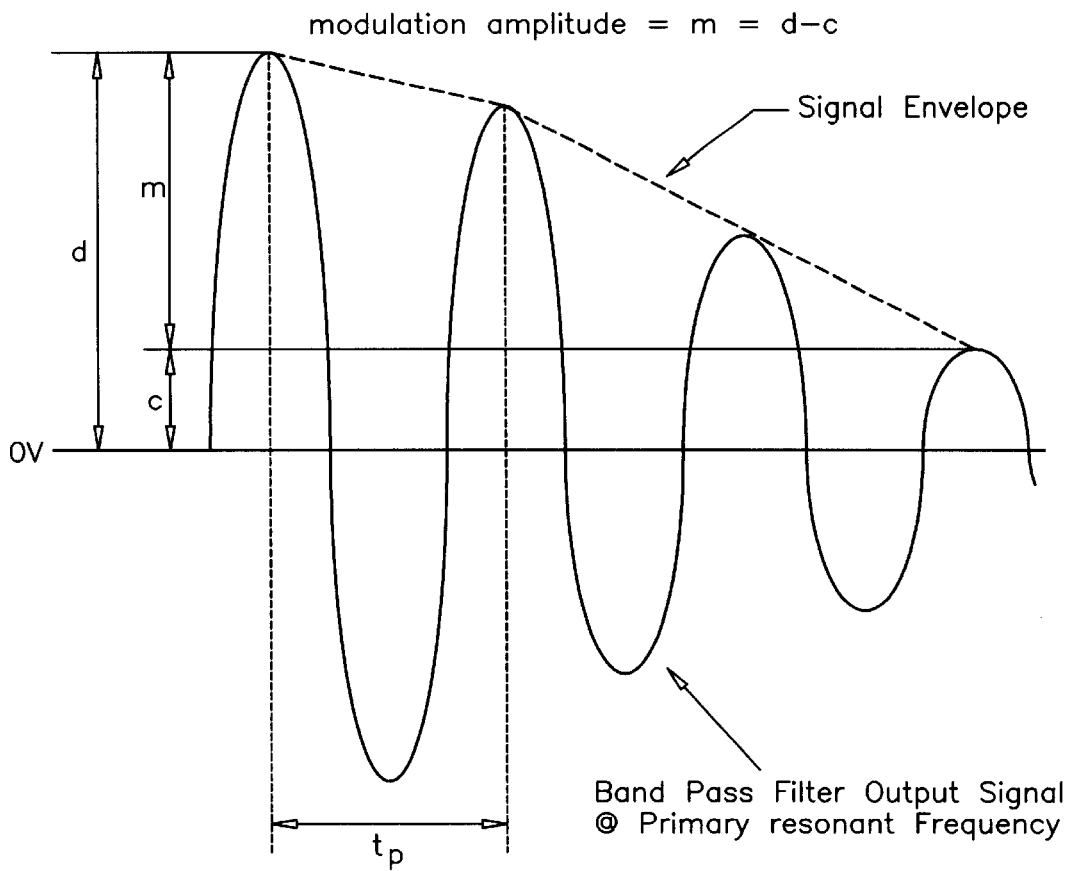
FIG. 7 is a graph illustrating "proper damping" of a stress wave signal at its resonant frequency in accordance with the present invention.

Stress wave analysis depends upon the modulation of sensor 20's resonant response. Thus, the damping of sensor 20 is preferred in the modulation amplitude at the frequency that can be obtained at the output of the ASC. The modulation amplitude "m" is defined as the amount of signal decay after a certain number of cycles, such as, but not limited, five cycles, following the initial excitation. As also seen in FIG. 6, after the certain number of cycles (i.e. 5), modulation amplitude "m" is less than fifty (50%) percent, of the original excitation amplitude "d". This small amount of modulation is preferably undesirable for the detection of multiple friction vents and the accurate measurement of their energy content. As such, the sensor 20 response shown in FIG. 6 is considered "under damped". A properly damped response in accordance with the present invention is illustrated in FIG. 7. The response is taken from a sensor 20 preferably with the same resonant frequency. FIG. 7 illustrates specifying damping at the resonant frequency, in addition to the Resonant Energy Integral. By damping relatively quickly (FIG. 7), additional shock and friction events will again modulate the signal.

Figure 10:
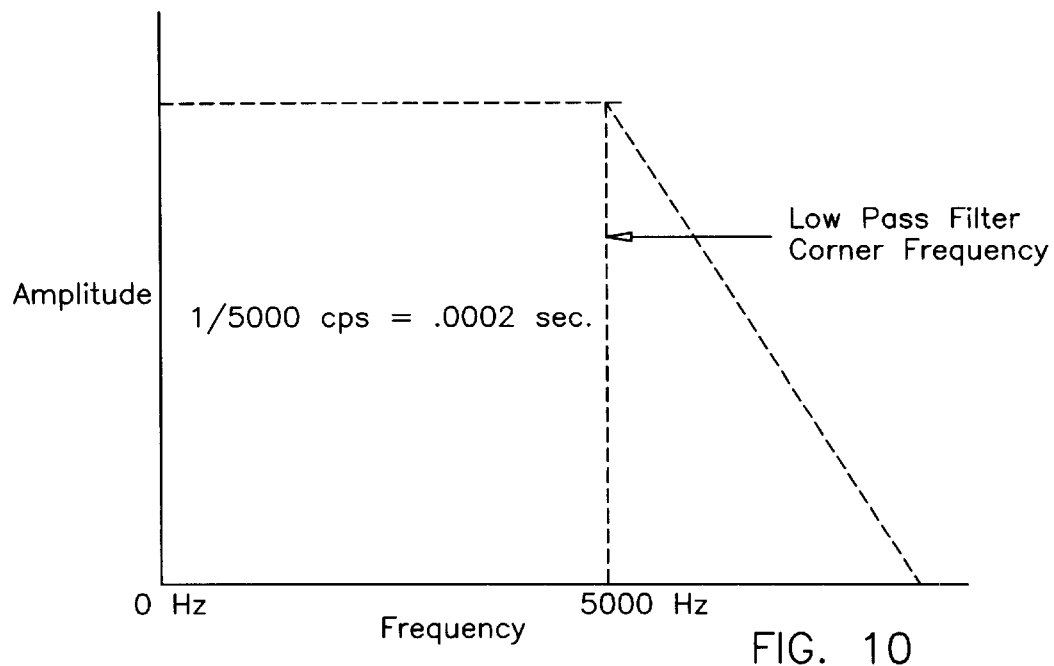
FIG. 10 is a graph illustrating a demodulator low-pass filter frequency response in accordance with the present invention.

FIGS. 8 and 9 illustrate the steps preferably involved in the demodulation portion of the stress wave analysis signal conditioning process. The damped sinusoidal output of the band pass filter is full wave rectified (FIG. 8), preferably prior to low pass filtering. The stress wave pulse train is defined as the demodulated output signal from the low pass filter (FIG. 9). The stress wave pulse train preferably has a frequency content from 0 Hz to the corner frequency of the low pass filter portion of the demodulation circuitry (See FIG. 10).

Sensor 20 can be used in monitoring many different applications (i.e. various shock and friction events from slow speed gear boxes to turbo machinery, etc.), such that its resonant output preferably decays to half amplitude in a specific number of cycles or less. The preferred number of cycles for decaying to half amplitude is five, though such number is not considering limiting and other numbers can be chosen and are considered within the scope of the invention. Furthermore,: sensor 20's resonant output preferably is not more than twenty (20%) percent, or some other determined value, of the initial response "d" in the number of cycles that occur during the time period that corresponds to the corner frequency of the low pass filter.

Figure 11:
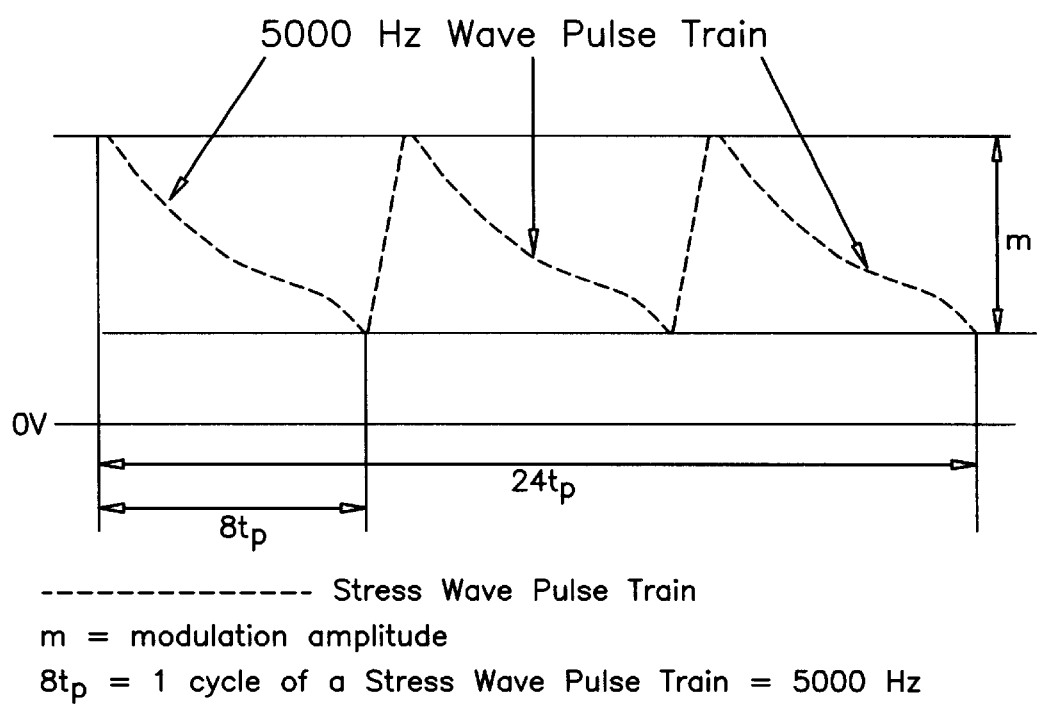
FIG. 11 is a graph illustrating a multiple event demodulator output in accordance with the present invention.

As an example, where a sensor 20 has a primary resonance of 40 KHz, the stress wave signal is preferably damped to less than twenty (20%) percent of its initial amplitude in eight (8) cycles. FIG. 11 illustrates a stress wave pulse train for the example, where the friction source excites sensor 20 at a periodic rate of five thousand (5000) times per second.

FIG. 12 illustrates the major components of one embodiment for a sensor 20 in accordance with the present invention. However other components can be used and are considered within the scope of the invention.

Accordingly, with the present invention the design of stress wave sensor 20 is preferably intimately related to the analog signal conditioning employed to extract the stress wave pulse train signal from broadband sources of excitation that contain in addition to the desired friction and shock events, vibration, audible noise and high frequency acoustic emissions. Sensor 20's design can also be a function of available calibration test equipment. The transducing element 24 of sensor can be a piezoelectric crystal, or can be based upon Micro Electrical Mechanical Systems (MEMS) technology, or other transducer technology. Sensor 20 preferably satisfies the following three criteria:

(a) has a resonant gain of approximately 30 db, at its primary resonant frequency, to assure adequate selective amplification of stress waves;

(b) provide a total energy content of the Resonant Energy Integral within a specified tolerance band (i.e. +/−10% of a standard value) and which can be measurable using standard test equipment and fixtures to produce calibration data that is traceable to recognized standards; and (c) have its resonant output decay to half amplitude in five cycles or less, and be down to no more than twenty (20%) percent of the initial response in the number of cycles that correspond to the corner frequency of the band pass filter.

Stress wave sensors 20 communicate with an electronic assembly which processes the stress wave signal(s) received from sensor(s) 20. The electronic assembly is in communication with sensors 20 via conventional cabling. In lieu of conventional cabling, the sensors can communicate with the electronics through wireless technology. .

In one embodiment, sensor 20 can include amplification, band pass filtering and demodulation of the stress wave signal at the sensing element. Alternatively, a non-amplified sensor 20 can also be used, preferably with the use of greater stress wave signal amplification outside the sensing element and a lower noise floor than the preferred-amplifying and filtering sensor. Preferably, the stress wave frequency of interest ranges from 20 KHz up. However, other values and ranges can be used and/or analyzed and all are considered within the scope of the invention. To reduce the stress wave signal amplitude range and the signal conditioning electronics' sensitivity sensor 20 may incorporate two features: gain and band pass filtering.

Sensor 20 is suitable for use in many applications that require the detection of an impact event within operating machinery, and all of such applications are considered within the scope of the invention.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A stress wave sensor in communication with an electronic assembly, said sensor comprising:

a transducing element generating a primary resonant frequency;

a charge converter in communication with said transducing element; and a high pass filter in communication with said charge converter for attenuating received signals that fall below, a selected frequency;

wherein said sensor having a resonant gain of approximately 30 db at its primary resonant frequency to allow for selective amplification of stress waves;

wherein said sensor having a resonant output of a specific amplitude, said resonant output decaying to half amplitude by a predetermined number of cycles.

2. The stress wave sensor of claim 1 wherein said predetermined number of cycles is five.

3. The stress wave sensor of claim 1 wherein said resonant output having a peak amplitude of a certain initial value which is reduced to not more than approximately twenty percent of the initial value in a number of cycles that occur during a time period corresponding to a corner frequency of a low pass filter associated with the electronic assembly.

4. The stress wave sensor of claim 1 wherein said selected frequency is approximately 20 KHz.

5. The stress wave sensor of claim 1 wherein said primary resonant frequency is above a natural vibration frequency of a monitored device.

6. The stress wave sensor of claim 1 wherein said transducing element is a piezoelectric crystal.

7. The stress wave sensor of claim 6 further including a body member wherein said piezoelectric crystal is mounted within said body member by at least one restraint member.

8. The stress wave sensor of claim 7 wherein said charge converter and said high pass filter are also disposed within said body member.

9. The stress wave sensor of claim 1 wherein said transducing element is a micro electrical mechanical system.

10. The stress wave sensor of claim 1 wherein the stress waves are from mechanical impacts which represent friction and shock events in operating machinery.

11. A stress wave sensor in communication with an electronic assembly used for stress wave analysis, said electronic assembly including a band pass filter, said sensor comprising:
- a transducing element generating a primary resonant frequency approximately between 35 KHz to 40 KHz;
- a charge converter in communication with said transducing element; and
- a high pass filter in communication with said charge converter for attenuating received signals that fall below a frequency of approximately 20 KHz;
- wherein said sensor having a resonant gain of approximately 30 db at its primary resonant frequency to allow for selective amplification of stress waves;
- wherein said sensor having a resonant output of a specific amplitude, said resonant output decaying to half amplitude by a predetermined number of cycles.

12. The stress wave sensor of claim 11 wherein said predetermined number of cycles is five.

13. The stress wave sensor of claim 11 wherein said resonant output having a peak amplitude of a certain initial value which is reduced to not more than approximately twenty percent of the initial value in a number of cycles that occur during the time period corresponding to a corner frequency of a low pass filter associated with the electronic assembly.

14. The stress wave sensor of claim 1 wherein said transducing element is a piezoelectric crystal.

15. The stress wave sensor of claim 14 further including a body member wherein said piezoelectric crystal is mounted within said body member by at least one restraint member.

16. The stress wave sensor of claim 15 wherein said charge converter and said high pass filter are also disposed within said body member.

17. The stress wave sensor of claim 11 wherein said transducing element is micro electrical mechanical system.

18. A stress wave sensor in communication with an electronic assembly, said sensor comprising:
- a transducing element generating a primary resonant frequency;
- a charge converter in communication with said transducing element; and
- a high pass filter in communication with said charge converter for attenuating received signals that fall below a selected frequency;
- wherein said sensor having a resonant gain of approximately 30 db at its primary resonant frequency and a resonant output of a specific amplitude, said resonant output decaying to approximately half amplitude by a predetermined number of cycles.

19. A stress wave senor in communication with an electronic assembly, said senor comprising;
- a transducing element generating a primary resonant frequency;
- a charge converter in communication with said transducing element; and
- a high pass or band pass filter in communication with said charge converter for attenuating received signals that fall below a selected frequency prior to any amplification of the received signals to prevent saturation of any signal conditioning amplification outside of the sensor;
- wherein the received signals includes a low frequency component and a high frequency component; wherein said high pass or band pass filter attenuates said low frequency component so that the high frequency component represents a significant percentage of the filtered signal prior to any subsequent amplification outside of the sensor.

20. The stress wave sensor of claim 19 wherein said sensor having a resonant gain of at least approximately 30 db at its primary resonant frequency to allow for selective amplification of stress waves received from mechanical impacts.

21. The stress wave sensor of claim 19 wherein said band pass filter also attenuates received signals which are above a second selected frequency.

22. The stress wave sensor of claim 21 wherein second selected frequency is approximately 125% of a primary resonant frequency of said transducing element.

* * * * *